United States Patent
Feygin et al.

[19]

[11] Patent Number: 5,952,240
[45] Date of Patent: Sep. 14, 1999

[54] DISCRETE MATRIX PLATE POSITIONER

[75] Inventors: Ilya Feygin, Mountainside; Rhett L. Affleck, Lawrenceville; Leslie A. Walling, Somerset, all of N.J.

[73] Assignee: Pharmacopeia, Inc., Princeton, N.J.

[21] Appl. No.: 08/926,389

[22] Filed: Sep. 9, 1997

[51] Int. Cl.$^6$ .................................................. G01N 35/00
[52] U.S. Cl. .............................. 436/180; 436/43; 436/47; 436/49; 422/63; 422/65; 422/100; 422/104; 435/288.3; 435/288.4; 414/749; 414/750
[58] Field of Search .................................. 436/43, 47, 49, 436/174, 180; 422/63, 65, 100, 104; 435/286.1, 286.2, 286.3, 288.4; 206/559, 522; 414/748, 750

[56] References Cited

U.S. PATENT DOCUMENTS

| | | | |
|---|---|---|---|
| 4,478,094 | 10/1984 | Salomaa et al. | 73/863.32 |
| 4,673,657 | 6/1987 | Christian | 436/501 |
| 5,096,670 | 3/1992 | Harris et al. | 422/65 |
| 5,104,621 | 4/1992 | Pfost et al. | 422/67 |
| 5,108,703 | 4/1992 | Pfost et al. | 422/65 |
| 5,206,171 | 4/1993 | Dillon et al. | 435/293 |
| 5,290,521 | 3/1994 | DeStefano, Jr. | 422/99 |
| 5,591,646 | 1/1997 | Hudson et al. | 436/518 |
| 5,779,985 | 7/1998 | Sucholeiki | 422/128 |
| 5,840,256 | 11/1998 | Demers et al. | 422/102 |

*Primary Examiner*—Long V. Le
*Attorney, Agent, or Firm*—Law Offices of Peter H. Priest

[57] ABSTRACT

A positive displacement positioner employs rigid stops and actuators to position a work piece, such as a microtiter plate, in any one of at least three positions. Positioner platforms, each of which is capable of moving a work piece between at least two distinct positions, are nested in order to multiply the number of positions available. For example, a two-position rigid stop positioner platform nested in a four-position rigid stop positioner platform, or a four-position rigid stop positioner platform nested in a two-position rigid stop positioner platform would permit the movement of a work piece to any one of eight distinct positions. A four-position platform nested inside a four-position platform yields sixteen positions, and so on. Each positioner platform preferably has a symmetrical polygonal outline and nested platforms provide displacement along each of the polygon's axes of symmetry. Consequently, a positioner will preferably provide displacement to any one of a number of positions.

29 Claims, 4 Drawing Sheets

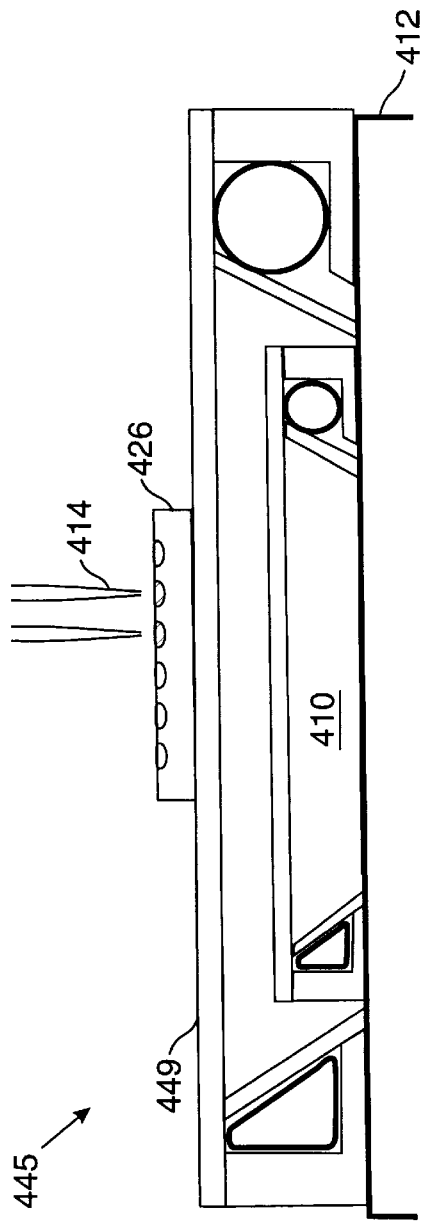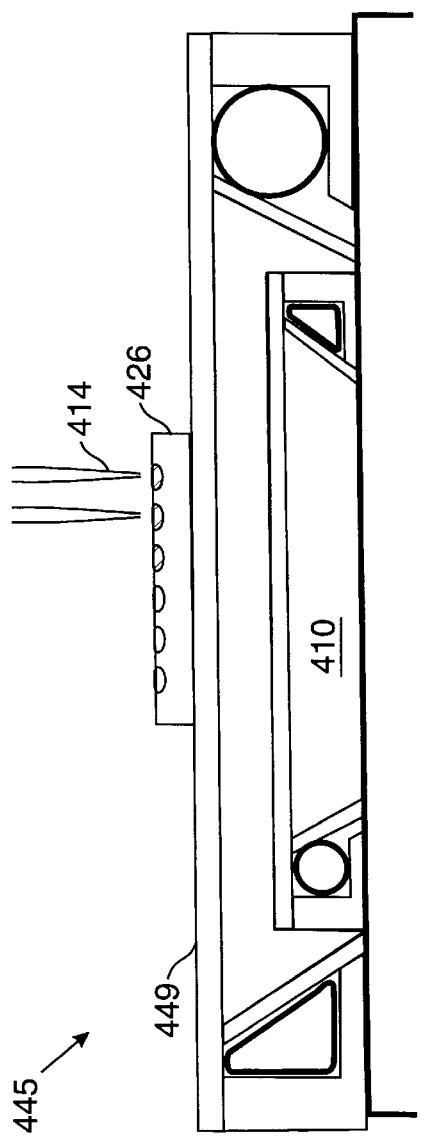

DISCRETE MATRIX PLATE POSITIONER

BACKGROUND OF THE INVENTION

1. Field of the Invention

The present invention is generally related to the positioning of work pieces and, in particular, to the positioning of microtiter plates in a liquid handling system.

2. Description of the Related Art

A wide variety of positioning systems are employed to bring vessels of various sorts into a desired position, where the vessels may receive various reactants, reagents, solvents or other fluids, for example. In particular, positioning systems are widely employed in the field of chemical synthesis and analysis. Plates which contain a multiplicity of small wells or vessels, often referred to as microtiter plates, are positioned under multi-tip dispensers to receive fluids from the dispensers, with each well in the plate receiving fluid from one dispenser tip at a time. Positioning systems range from the very complex, which require sophisticated computer control systems coupled to a complex series of actuators or robotic systems, to relatively simple positive displacement systems which move a work piece, vessel, or similar item against a rigid stop.

The more complex systems provide the advantage of greater placement flexibility. In the field of chemical synthesis and analysis, such flexibility may allow a robot arm with an attached pipette to extract a sample from one of several reservoirs, transport the sample to any one of hundreds, or even thousands, of reaction wells located within a microtiter plate, and release the sample into the well. However convenient such a system may be, the complexity of such a system leads to greater expense. Furthermore, since the robot arm, or other pipette-holding mechanism, must be carefully accelerated and decelerated many times over, there are many opportunities for mispositioning the pipette. Additionally, such a positioner's movements are typically comparatively slow, since the positioner must be carefully accelerated and decelerated in order to position the pipette properly. The complexity of such a positioning system also introduces the possibility of multiple failure mechanisms. Therefore, reliability and maintenance can be major issues with such a positioning system.

On the other hand, positive displacement positioning systems, which displace a work piece against a rigid stop, tend to be much simpler, much less expensive, and more reliable than a complex positioner such as the ones just described. Nevertheless, while positive displacement, or rigid stop, positioners typically provide highly accurate positioning, the typical rigid stop positioner provides a maximum of only four discrete positions, which may be described as top-left, top-right, bottom-left and bottom-right, that is, four positions defined by two rigid stops in either of two orthogonal axes. Such a positioner may be employed, for example, to translate a 384 well microtiter plate under a standard 96-tip dispenser and thereby allow the 96 tips of the dispenser to engage with one of four distinct 96-member sets of wells within the microtiter plate. Although the simplicity, reliability, and relative low cost of rigid stop positioners make them highly desirable, their limited positioning capabilities severely restrict their application.

Many applications, particularly in the field of combinatorial chemical synthesis, would benefit from the ability to position work pieces such as microtiter plates in more than just four discrete positions. For example, microwell plates having 1,536 wells are available for use. When using a currently widely used 96-tip dispenser, a minimum of sixteen positions would be required to access all the wells within such a plate. At the same time, it would be highly desirable to retain the simplicity, reliability and low cost that a rigid stop positioning system can offer.

SUMMARY OF THE INVENTION

The present invention is directed to accurate, inexpensive positioning systems which, in spite of their relative simplicity and consequential low cost and high reliability, are capable of providing greater positioning flexibility than conventional rigid stop positioners.

The invention addresses the above problems by providing a positive displacement positioner which includes nested positioner platforms, each of which is capable of providing at least two-position displacement. In one aspect, the invention comprises nested rigid stop linear positioner platforms. In a preferred embodiment, the positioner employs rigid stops and actuators to position a work piece, such as a microtiter plate, in any one of at least four positions. By nesting the positioner platforms, the number of positions available are the product of twice the number of a platform's symmetrical axes. For example, a two-position rigid stop positioner platform nested in a four-position rigid stop positioner platform, or a four-position rigid stop positioner platform nested in a two-position rigid stop positioner platform would permit the movement of a work piece to any one of eight distinct positions. Each positioner platform preferably has a symmetrical polygonal outline with nested platforms providing displacement along each of the polygon's axes of symmetry. Consequently, a positioner will preferably provide displacement to any one of $(2A)^N$ positions, where N is the number of platforms, and A is the number of the polygon's axes of symmetry. The travel of each successive platform is preferably equal to twice that of its nested platform, thereby eliminating overlap and maximizing the number of positions available.

These and other features, aspects and advantages of the invention will be apparent to those skilled in the art from the following detailed description, taken together with the accompanying drawings.

BRIEF DESCRIPTION OF THE DRAWINGS

FIGS. 4A and 4B illustrate an inverted embodiment of the presently preferred sixteen-position nested rigid stop positioner. The two views demonstrate movement to the left due to operation of the nested positioner's actuator.

DETAILED DESCRIPTION

A nested positioner in accordance with the present invention preferably provides accurate, inexpensive positioning by providing a positive displacement positioner which includes nested positioner platforms, each of which is capable of placing a work piece in, e.g., either of two positions. The inventive positioner suitably includes nested rigid stop linear positioner platforms, with each additional nested platform multiplying the number of positions available by the number of positions it provides. For example, a four-position platform nested within a four-position platform makes sixteen-position placement possible and, by nesting the resulting sixteen-position platform within a four-position platform, a sixty-four-position platform is produced. As noted in the background section above, a sixteen-position positioner could be employed in conjunction with a 96-tip dispenser to access all the cavities with-n a 1536 well microtiter plate. Such a microtiter plate is disclosed in copending U.S. provisional application 60/037,636, filed Feb. 18, 1997, entitled Multi-Well Plate, which is hereby incorporated by reference.

In the presently preferred embodiments, the travel of each successive platform is preferably equal to twice that of its nested platform, thereby eliminating position overlap and maximizing the number of positions available. It will be recognized that for applications where overlap is desired it may readily be provided and a combination of overlapping and nonoverlapping platforms may be employed, for example, to service a standard 864 well plate using a standard 96-tip dispenser. In the descriptions that follow, directions, such as left, right, top and bottom are employed for clarity of exposition and refer to directions relative to a viewer of the figures, but should not be construed to limit the orientation of the illustrated embodiments of the invention.

Figure 1:
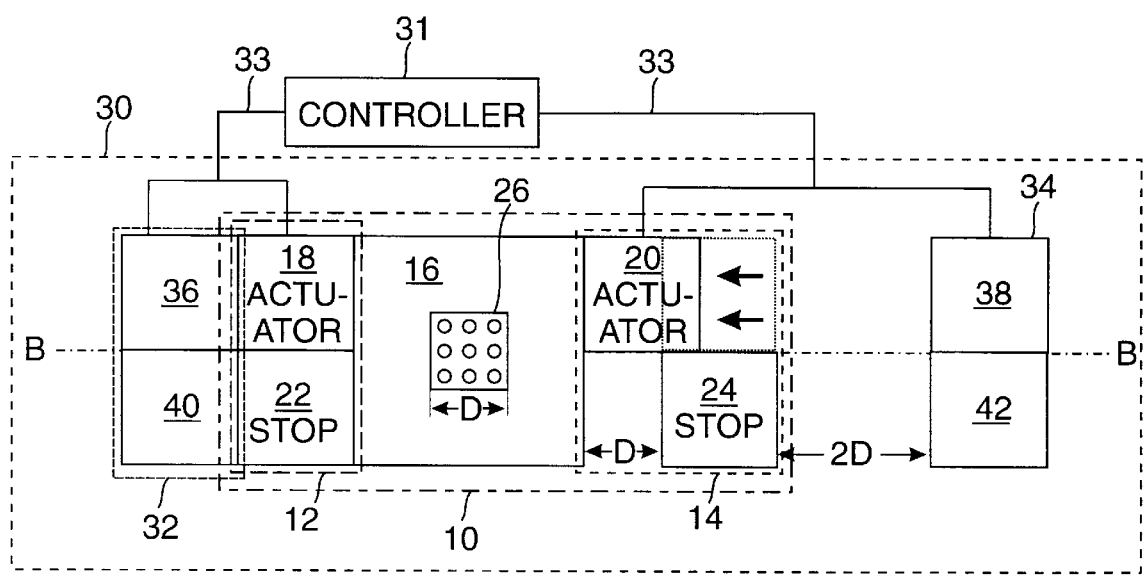
FIG. 1 is a block diagram which illustrates the basic components of a simple nested rigid stop positioner according to the present invention which provides translational movement to a platform along one axis.

The block diagram of FIG. 1 illustrates one embodiment of a positioner platform 10 in accordance with the present invention. The positioner platform 10 includes left and right actuator/stop combinations 12 and 14, respectively, connected to a platform 16. Left and right actuator/stop combinations include actuators 18 and 20, respectively, which may be piston-driven, gear-driven or other linear actuators, and rigid stops 22 and 24, respectively, which limit the translational motion of the platform 16. In some cases, for example, when a piston driven actuator which is either fully extended or fully retracted is employed, each actuator may inherently include a stop. In other cases a physical impediment may be employed to terminate translational motion. The left actuator 18 is connected to translate the platform 16 to the right as far as the right stop 24 and the right actuator 20 is connected to translate the platform 16 to the left as far as the left stop 22. The platform 16 typically will be employed to position a work piece, such as a microtiter plate 26 shown resting or top of the platform 16, using translational motion along an axis of symmetry B.

The platform 10 is nested within another platform 30 which includes a left actuator/stop 32 and a right actuator/stop 34 each of which includes an actuator, 36 and 38, and stop 40 and 42, respectively. The actuator/stop combinations 32 and 34 operate in the same manner described above in reference to the actuator/stop combinations 12 and 14. However, the actuator/stop combinations 32 and 34 are connected to translate the entire positioner platform 10. In order to provide the maximum number of positions without overlap, the travel of the inner actuators 18 and 20 is equal to the width d of the plate 26 and the travel of the outer actuators 36 and 38 is equal to 2d, twice the width of the plate 26. In this manner, the illustrated nested positioning platforms provide four distinct non-overlapping positions: an initial, illustrated, position with both of the right actuators 20 and 38 completely extended and both of the left actuators 18 and 36 completely retracted, and three other positions resulting from combinations of retraction and extension of the actuators 36, 18, 20 and 38. The platform 30, may itself be nested within another platform which may itself be nested in another platform, and so on, to provide more positions. A controller 31, which, in the presently preferred embodiment, includes a microprocessor and program memory, is connected through control lines 33 to control the actuator stops. The program memory preferably stores a program which controls positioning of the plate 26 with respect to a multi-tip dispenser to suitably add reagents to each of the wells.

Figure 2:
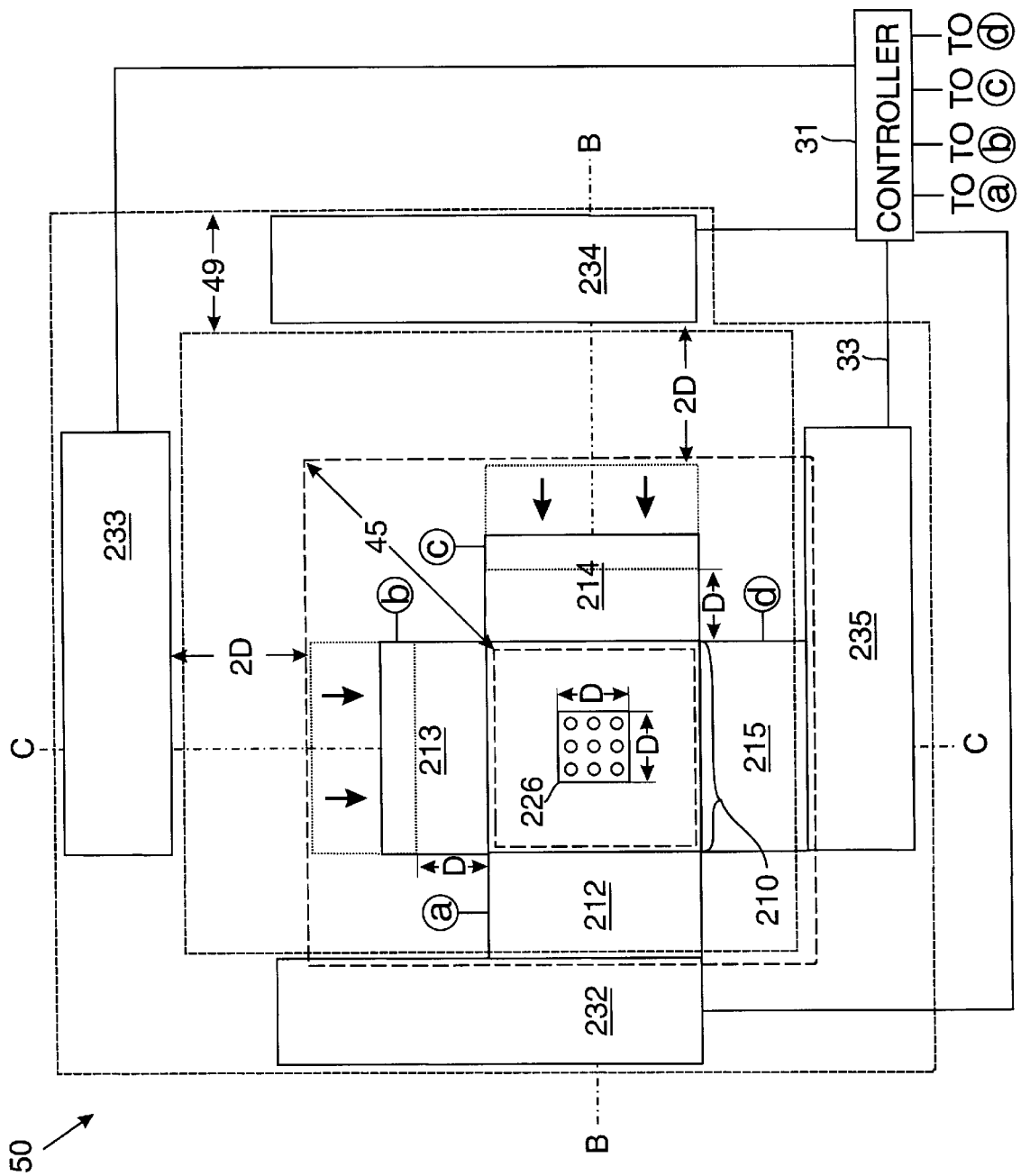
FIG. 2 is a block diagram of a nested rigid stop positioner which provides translational movement to a platform along two orthogonal axes.

A nested positioner 50 which provides translation along two axes of symmetry B and C is illustrated in the block diagram of FIG. 2. Actuator/stops 212, 214, 232, and 234 may be the same as actuator/stops 12, 14, 32, and 34 described in relation to FIG. 1. Additionally, a platform 210 and plate 226 may be the same as the platform 10 and plate 26, described in relation to FIG. 1. Actuator/stops 213, 233, 215 and 235 are connected to provide translational motion along the axis C which is perpendicular to the left-right translational axis B. Although the positioner 50 has a rectangular outline, the invention contemplates positioners having any polygonal outline and translational motion along any of the polygon's axes of symmetry, such as the axes B and C. The travel of positioners 213 and 233 are preferably related to the width D of the plate 226, or the active area thereof, with the travel of actuator/stops 215 and 213 equal to D and that of actuator/stops 235 and 233 equal to 2D. The positioner 50 includes nested platforms 45 and 49. Nested platform 45 includes platform 210, actuator/stops 212, 213, 214, and 215, and platform 49 includes actuator/stops 232, 233, 234, and 235. The positioner 50 provides sixteen discrete positions: twice the number of nested platforms, 45 and 49, times twice the number of symmetrical axes, B and C, along which translational motion is provided.

Figure 3:
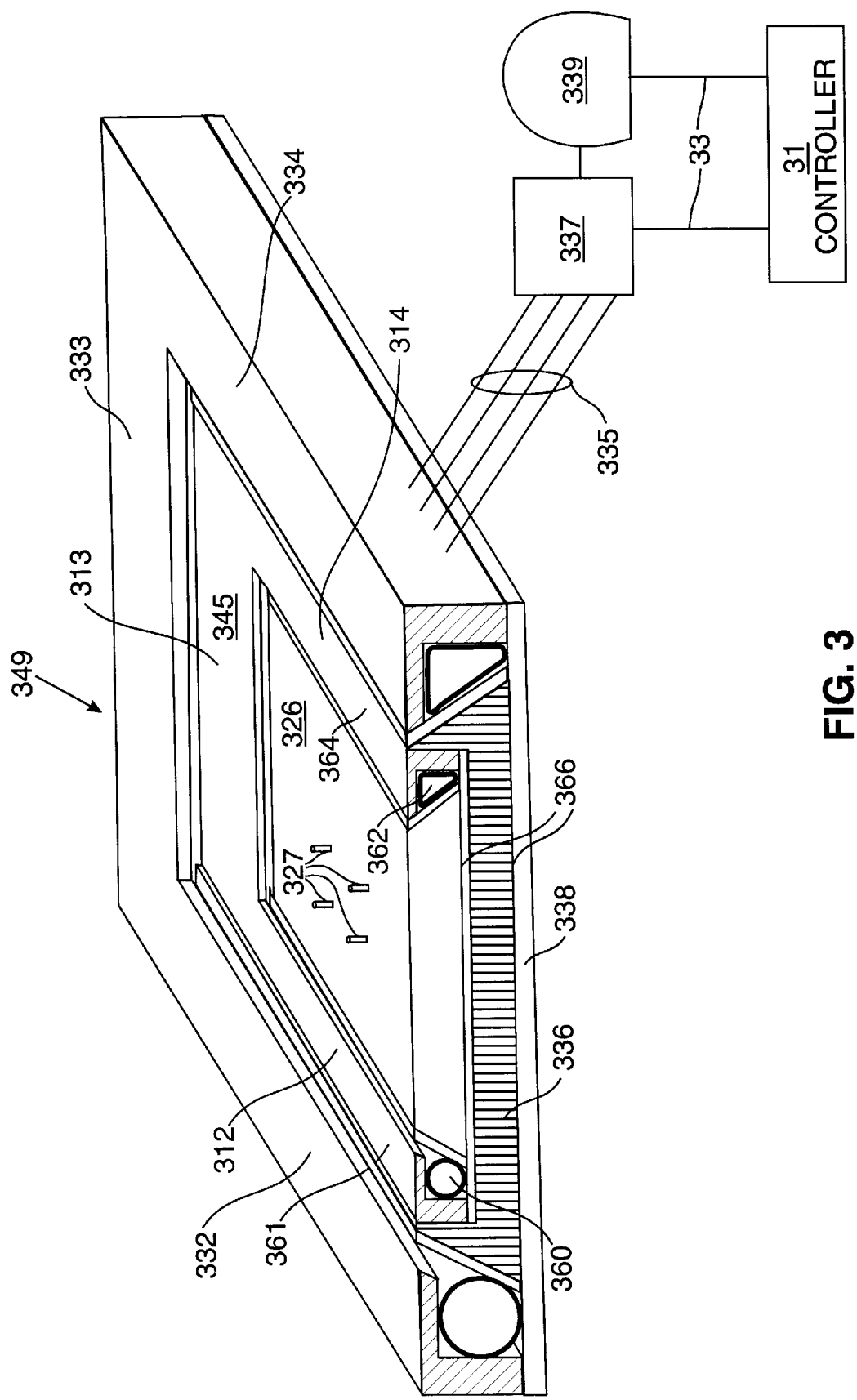
FIG. 3 is a sectional view of a presently preferred embodiment of a sixteen-position nested rigid stop positioner according to the present invention.

The presently preferred actuator/stops are illustrated in the sectional view of a rectangular embodiment of a positioner shown in FIG. 3. A positioner platform 345 includes a platform * 326 which is coupled to actuator/stops 312, 313, 314 and 315 (not shown in this view) and nested in a platform 349 which includes actuator/stops 332, 333, 334 and 335 (not shown in this view). The platform 349 also includes a movable support platform 336 which rests on a stationary support platform 338 and supports the nested positioner platform 345. Each of the actuator/stops 312–315 and 332–335 include similar features which will be discussed in detail in relation to actuator/stop 312 and 314. A flexible bladder 360 is positioned between the platform 326 and a stop 361. When filled with fluid, the bladder 360 expands to move the platform 326 generally to the right in FIG. 3. At the same time, fluid is evacuated from a corresponding bladder 362 included in the actuator/stop 314, which also includes a stop 364. Fluid may be pumped in and out of the bladders in a conventional manner. For example fluid may be displaced from one bladder by the expansion of the opposing bladder. With the bladder 360 pumped substantially full and the bladder 362 substantially empty, the platform 326 will be translated against the stop 364. Similarly, with the bladder 362 substantially full and the bladder 360 substantially empty, the platform 326 will be translated against the stop 361. The contact surfaces 366 are preferably low friction surfaces and may include bearings or may be composed of low surface friction materials such as Teflon™, available from Dupont Corporation. A work piece such as a microtiter plate will preferably be held in place on the top surface of the platform 326, for example by studs 327 which provide registration for the work piece, thereby insuring that the translational motion of the positioner is translated into movement of the work piece to the desired sixteen positions of this presently preferred embodiment of the positioner.

In this preferred embodiment, each of the bladders is connected through a fluid line 335 to a valve system 337 which is, in turn, connected to one or more pumps 339. The controller 31 is connected through control lines 33 to the pump 339 and valve system 337 to control the previously described evacuation and filling of the bladders in a manner which suitably positions a workpiece. The positioned workpiece may be a microtiter plate, such as the previously mentioned 1536-well plate, that is positioned to accept reagents from a 96-tip dispenser, or the 96-tip dispenser may be the moved workpiece that is positioned to dispense reagents to a stationary 1536 well plate. Combinations of movement by two workpieces, for example, movement of a microtiter plate and a standard dispenser, are also contemplated by the present invention.

A work piece such as a microtiter plate 410 may alternatively be placed on the positioner as illustrated in FIGS. 4A and 4B, where the positioner 445 is "upside down" relative to the positioner 345 of FIG. 3. That is, a nested positioner platform 426 extends beyond a nesting positioner platform 449 to rest on a supporting surface 412 and the microtiter plate is held in place on the top surface of the nesting positioner platform 449 under an array of pipettes 414 which may be arranged in a standard pattern such as a square array of ninety six pipettes. Each of the positioner platforms includes bladder actuators, as described in detail in relation to FIG. 3. The operation of the actuators of platform 410 is illustrated by the two distinct positions of FIGS. 4A and 4B. With the right bladder of platform 410 inflated, the pipettes 414 are aligned with a group of wells within the microtiter plate 426, as illustrated in FIG. 4A. FIG. 4B illustrates the leftward shift of the entire positioner 445 when the right bladder of the positioner 410 is inflated and its left bladder is deflated. Due to the coplanar translational movement of the positioner 445, the pipettes 414, which are stationary, become aligned with a different group of wells within the microtiter plate 426. The illustrated positioner 445 is capable of positioning the plate 426 in any of four posit-ions, to the left and right in this view. With four positions along the axis going into the page, the total number of positions provided by the positioner 445 is sixteen.

The foregoing description of specific embodiments of the invention has been presented for the purposes of illustration and description. It is not intended to be exhaustive or to limit the invention to the precise forms disclosed, and many modifications and variations are possible in light of the above teachings. For example, as noted above, two-position pistons, or other mechanical linkages could be employed as actuator/stops for the new rigid stop nested positioners. The embodiments were chosen and described in order to best explain the principles of the invention and its practical application, to thereby enable others skilled in the art to best utilize the invention. It is intended that the scope of the invention be limited only by the claims appended hereto.

We claim:

1. A nested rigid stop positioner for positioning a work piece, comprising:
   a first rigid stop positioner, adapted to provide two-position translational movement to a work piece; and
   a second rigid stop positioner which nests with said first rigid stop positioner to provide two-position translational movement to said first positioner and to thereby provide a total of more than two available positions for positioning said work piece.

2. The nested positioner of claim 1, said nested rigid stop positioner has an outline shape which is a polygon having a axes of symmetry, where A is an integer greater than one.

3. The nested positioner of claim 2, wherein each of the first and second rigid stop positioners is a positioner which provides two-position translational motion along each of the axes of symmetry.

4. The nested positioner of claim 1, wherein each of the first and second rigid stop positioners provides two-position translational motion along at least two axes and the total number of positions into which the nested positioner may move a work piece is at least sixteen.

5. The nested positioner of claim 2, wherein the total number of positions into which the nested positioner may move a work piece is equal to the product of 4 times the number of rigid stop positioners that are nested and the number of axes of symmetry of the polygon which defines the outline of the nested positioner.

6. The nested positioner of claim 5, wherein each rigid stop positioner includes at least two actuators, two rigid stops and a platform, with said actuators, stops and platforms coupled to provide translational motion of said platforms to any one of 2A adjacent coplanar positions.

7. The nested positioner of claim 6, wherein each additional rigid stop positioner after said first rigid stop positioner is coupled to provide translational motion to the immediately preceding rigid stop positioner and to thereby provide translational motion of a work piece to any of $(2A)^N$ adjacent coplanar positions, where N is the total number of nested positioner platforms.

8. The nested positioner of claim 7, wherein each of said actuators comprises a pair of inflatable bladders coupled to provide translational movement in opposition to one another, with one bladder inflated as the other is deflated.

9. The nested positioner of claim 5, wherein the number of axes A is not the same for all of said nested positioners.

10. A nested rigid stop positioner, comprising:
    a first rigid stop positioner, including first and second actuators, first and second stops, and a first platform, with said actuators and stops coupled to said platform to provide two-position translational movement to said platform in each of two orthogonal coplanar directions, thereby providing four-position placement; and
    a second rigid stop positioner nested with the first rigid stop positioner, the second rigid stop positioner including third and fourth actuators, third and fourth stops, and a second platform, with said third and fourth actuators and third and fourth stops coupled to said second platform to provide two-position translational movement to said second platform in each of said two orthogonal directions, thereby providing four-position placement, said second platform being coupled to said first positioner to provide four-position placement to said first positioner and to thereby provide sixteen-position placement for said first platform.

11. The nested positioner of claim 10, wherein each of said actuators comprises a pair of inflatable bladders coupled to provide translational movement in opposition to one another, with one bladder inflated as the other is deflated.

12. A polygonal nested positioner, comprising:
    a plurality of nested two-position linear actuators coupled to positioning platforms to thereby provide translational movement to said platforms along the polygon's axes of symmetry such that a workpiece may be positioned in any one of at least two-positions for each of the polygon's axes of symmetry; and
    a plurality of corresponding rigid stops coupled to said platforms to determine the extent of translational movement available to each platform from said nested linear actuators.

13. The nested positioner of claim 12, wherein none of the available positions overlaps any other available positions.

14. The nested positioner of claim 12, wherein at least one available position overlaps with another available position.

15. A method of positioning a workpiece, comprising the steps of:

moving the workpiece with a first actuator rigid stop combination; and employing a second actuator rigid stop combination which nests with the first actuator rigid stop combination to move the first actuator rigid stop combination and to thereby move the workpiece.

16. A nested rigid stop positioner for selectively positioning a multi-well microtiter plate beneath a multi-tip reagent dispenser comprising:

a first rigid stop positioner, connected to provide two-position translational movement to the multi-well microtiter plate;

a second rigid positioner, nested with said first rigid stop positioner to provide two-position translational movement to said first positioner and to thereby provide a total of more than two available positions for positioning said plate.

17. The positioner of claim 16 wherein the multi-tip reagent dispenser has n tips arranged in a grid to discharge reagent or reagents substantially simultaneously into n-wells of the multi-well microtiter plate.

18. The positioner of claim 17 wherein the positioner can position the multi-well microtiter plate in at least m different positions in which n different wells are located beneath the multi-tip reagent dispenser.

19. The positioner of claim 18 wherein the multi-well microtiter plate has a total of mn wells.

20. The positioner of claim 16 wherein n equals 96.

21. The positioner of claim 18 wherein m equals an integer from 4 to 16.

22. A nested rigid stop positioner for selectively positioning a multi-well microtiter plate with respect to a multi-tip reagent dispenser comprising:

a first rigid stop positioner, including first and second actuators, first and second stops, and a first platform on which the multi-tip reagent dispenser is mounted, with said actuators and stops coupled to said platform to provide two-position translational movement to said platform in each of two orthogonal coplanar directions, thereby providing four-position placement; and a second rigid stop positioner nested with the first rigid stop positioner, the second rigid stop positioner including third and fourth actuators, third and fourth stops, and a second platform, with said third and fourth actuators and third and fourth stops coupled to said second platform to provide two-position translational movement to said second platform in each of said two orthogonal directions, thereby providing four-position placement, said second platform being coupled to said first positioner to provide four-position placement to said first positioner and to thereby provide sixteen-position placement for said first platform.

23. The positioner of claim 22 wherein the multi-tip reagent dispenser has 96 discrete tips for substantially simultaneously discharging a reagent or reagents.

24. The positioner of claim 22 wherein the multi-well microtiter plate has 1536 wells arranged in 16 grids of 96 wells.

25. A nested rigid stop positioner for selectively positioning a multi-well microtiter plate with respect to a multi-tip reagent dispenser comprising:

a first rigid stop positioner, including first and second actuators, first and second stops, and a first platform on which the multi-well microtiter plate is mounted, with said actuators and stops coupled to said platform to provide two-position translational movement to said platform in each of two orthogonal coplanar directions, thereby providing four-position placement; and a second rigid stop positioner nested with the first rigid stop positioner, the second rigid stop positioner including third and fourth actuators, third and fourth stops, and a second platform, with said third and fourth actuators and third and fourth stops coupled to said second platform to provide two-position translational movement to said second platform in each of said two orthogonal directions, thereby providing four-position placement, said second platform being coupled to said first positioner to provide four-position placement to said first positioner and to thereby provide sixteen-position placement for said first platform.

26. The positioner of claim 25 wherein the multi-tip reagent dispenser has 96 discrete tips for substantially simultaneous discharging a reagent or reagents;.

27. The positioner of claim 25 wherein the multi-well microtiter plate has 1536 wells arranged in 16 grids of 96 wells.

28. A method of discharging reagent from a multi-tip reagent dispenser into wells of a multi-well microtiter plate comprising the steps of:

moving the multi-well microtiter plate relative to the multi-tip reagent dispenser with a first actuator/rigid stop combination to a first position;

discharging reagent;

employing a second actuator/rigid stop combination which nests with the first actuator/rigid stop combination to move the first actuator/rigid stop combination and to thereby move the multi-well microtiter plate relative to the multi-tip reagent dispenser to a second position; and discharging reagent.

29. The method of claim 28 wherein the multi-tip reagent dispenser has n discrete tips and the multi-well microtiter plate has a total of mn wells arranged in m grids of n-wells, and the first and second actuator/rigid stop combinations are operated to move each of the m grids of n-wells beneath the n discrete tips of the multi-tip reagent dispenser.

* * * * *

UNITED STATES PATENT AND TRADEMARK OFFICE
CERTIFICATE OF CORRECTION

PATENT NO. : 5,952,240
DATED : September 14, 1999
INVENTOR(S) : Feygin et al.

It is certified that error appears in the above-identified patent and that said Letters Patent is hereby corrected as shown below:

Col. 3, line 10, delete "with-n" and insert --within--;

Col. 4, line 35, delete "*";

Col. 5, line 38, delete "posit-ions" and insert --positions--;

Col. 5, lines 66-67, delete "a axes" and insert --A axes--; and

Col. 8, line 33, delete ";".

Signed and Sealed this

First Day of August, 2000

Attest:

Q. TODD DICKINSON

Attesting Officer

Director of Patents and Trademarks